United States Patent [19]

Katsoulis et al.

[11] Patent Number: 5,608,096

[45] Date of Patent: Mar. 4, 1997

[54] METHOD OF FORMING SILOXANE POLYMERS USING A HETEROPOLY CATALYST HAVING A KEGGIN STRUCTURE

[75] Inventors: Dimitris E. Katsoulis; John R. Keryk, both of Midland, Mich.

[73] Assignee: Dow Corning Corporation, Midland, Mich.

[21] Appl. No.: 580,417

[22] Filed: Dec. 28, 1995

[51] Int. Cl.⁶ ........................................... C07F 7/08
[52] U.S. Cl. ............................ 556/462; 528/19
[58] Field of Search ..................... 556/462; 528/19

[56] References Cited

U.S. PATENT DOCUMENTS 5,173,558  12/1992  Hansen et al. .................. 556/462 X
5,354,830  10/1994  Williams ........................ 556/462 X

OTHER PUBLICATIONS

Misono, M. "Heterogeneous Catalysis by Heteropoly Compounds of Molybdenum and Tungsten", Catal. Rev.–Sci. Eng., 29(2&3), 269–321 (1987).
Chemistry & Technology of Silicones, [239] 5.4, pp. 209–233 (1968). (Noll).

*Primary Examiner*—Paul F. Shaver
*Attorney, Agent, or Firm*—Patricia M. Scaduto

[57] ABSTRACT

The invention relates to a method of forming siloxane polymers using a heteropoly catalyst having a Keggin structure. The method comprises contacting a fluid comprising at least one siloxane polymer precursor selected from the group consisting of cyclic siloxanes (I) having the formula $(RR'SiO)_a$ and linear siloxanes (II) having the formula

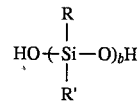

where R is a substituted or unsubstituted monovalent hydrocarbon having from 1 to 6 carbon atoms, R' is hydrogen or a substituted or unsubstituted monovalent hydrocarbon having from 1 to 6 carbon atoms, a is at least 3 and b is at least 1; with an effective amount of a heteropoly catalyst having a Keggin structure, selected from the group consisting of heteropoly acids (III) having the formula $H_nXM_{12}O_{40}$, salts thereof and mixed acid-salts thereof, where X is $B^{+3}$, $Si^{+4}$, $Ge^{+4}$, $P^{+5}$, M is $Mo^{+6}$ and n is 3, 4 or 5, as required for the valence of the heteropoly acid to equal 0, at a temperature ranging from about 23° C. to the boiling point of the siloxane polymer precursor.

16 Claims, No Drawings

METHOD OF FORMING SILOXANE POLYMERS USING A HETEROPOLY CATALYST HAVING A KEGGIN STRUCTURE

BACKGROUND OF THE INVENTION

1. Field of Invention

This invention relates to a method of forming siloxane polymers using a heteropoly catalyst having a Keggin structure.

2. Background Information

Many methods for forming linear siloxane polymers have been described in the art. See for example Noll, W., *Chemistry and Technology of Silicones*, Academic Press, Inc. 1968, pp. 209–233. In general, ring-opening polymerization of cyclodialkylsiloxanes, considered to be a chain growth process, can be initiated by either acids, such as acid clays, HF, $H_2SO_4$, $CF_3SO_3H$, etc. or bases, such as GOH, GOSi≡, GOR, GR etc., where G is an alkali metal or quaternary ammonium or phosphonium group and R (depending on G) is an alkyl, polystyryl or poly(trimethylsilylvinyl) group. Step growth polymerization in linear polysiloxanes often consists of homocondensations of silanol-ended siloxanes catalyzed by either strong acids or bases or mild amines or carboxylic acids combined with quaternary ammonium salts. Termination of both chain growth and step growth polymerization is usually effected by neutralization of the acid or base.

Nevertheless, there are some disadvantages to these methods of forming siloxane polymers. One disadvantage is that branching, often described as "T" branching often occurs with these methods due to cleavage of R—Si groups. It has been found, for example, that siloxane polymers having an average degree of polymerization of 200 have on average about one "T" branch per polymer chain. Another disadvantage is that neutralization of the acid or base is required in order to terminate the polymerization reaction. This is an additional step which can poison the catalyst and cause additional waste products. In addition, unless all traces of acid or base are eliminated, the reverse reaction may be catalyzed. Further, the catalyst may not be easily recoverable.

The literature describes certain catalytic effects of inorganic metal-oxygen clusters, see for example Misono, M., *Catal. Rev. Sci. Eng.*, 1987, 29, 269. These clusters are referred to in the literature as "isopolyanions" when only a polyvalent metal and oxygen are involved and can be represented by the formula $(M_mO_y)^{p-}$. If an additional metallic or non-metallic element is present, these clusters are referred to as "heteropolyanions" and can be represented by the formula $(X_xM_mO_y)^{q-}$.

In the formulae described above, M is a polyvalent metal such as molybdenum, tungsten and less frequently vanadium; X is the "heteroatom" and can be almost any element in the periodic table, other than a noble gas; O is oxygen; x, m, and y are integers where x<<m and p and q represent the charge on the anion. When x=1, m=12 and y=40, the heteropolyanion usually adopts what is known as the Keggin structure. With this Keggin structure, the central heteroatom in a $XO_4$ tetrahedron is surrounded by 12 $MO_6$ octahedra that share edges and corners to form a heteropolyanion with an overall tetrahedron symmetry.

The heteropolyanions are typically negatively charged and so easily associate with various cations, including hydrogen, alkali metals, alkaline earth metals and ammonium cations. When hydrogen is the cation, heteropoly acids are formed. Salts may be formed by adding any of the other types of cations described above and acid-salt mixtures are obtained when both hydrogen and other types of cations are present. The addition of appropriate amounts of the various cation(s) having positive charges will balance the negative charge of the anion so that the overall valence of the heteropoly compound is zero. These neutral heteropoly compounds when m is 12 and y is 40 are referred to herein as "heteropoly catalysts having a Keggin structure" or "heteropoly catalysts."

These heteropoly catalysts having a Keggin structure are particularly suitable for catalysis reactions because they are stable in solution and in solid form. Large scale industrial processes using heteropoly catalysts, include, hydration of propene, oxidation of methacrolein and polymerization of tetrahydrofuran.

The main advantages of heteropoly catalysts and heteropoly acids in particular, over traditional protic acids such as sulfuric acid, hydrochloric acid, hydrofluoric acid, etc are their versatility towards catalytic molecular design and their low environmental hazard.

The former advantage is due to the heteropoly catalyst having at least three parts a cationic part, an anionic part and a solvation sphere. Altering any of these parts can produce a catalyst having different surface activity, charge and reactivity.

In addition to their versatility, heteropoly catalysts are important because they are easily recovered, recrystallized if necessary, and reused. The catalysis can be terminated at will without having to use neutralization steps that can poison the catalyst and create additional waste products.

One of the objectives of the method of the present invention is the preparation of siloxane polymers from siloxane polymer precursors which have less branching than siloxane polymers produced by other methods. Another objective of the method of this invention is to form siloxane polymers using a catalyst which does not require neutralization.

SUMMARY OF THE INVENTION

The objectives of this invention can be achieved by forming siloxane polymers using a heteropoly catalyst having a Keggin structure. The method comprises contacting a fluid comprising at least one siloxane polymer precursor with a heteropoly catalyst having a Keggin structure. This method is effective for opening siloxane ring structures also known as cyclic siloxanes and chain extension of the opened ring structures and of linear siloxanes.

DETAILED DESCRIPTION OF THE INVENTION

The invention relates to a method of forming siloxane polymers, the method comprising contacting a fluid comprising at least one siloxane polymer precursor selected from the group consisting of cyclic siloxanes (I) having the formula $(RR'SiO)_a$ and linear siloxanes (II) having the formula

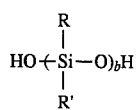

where R is a substituted or unsubstituted monovalent hydrocarbon having from 1 to 6 carbon atoms, R' is hydrogen or a substituted or unsubstituted monovalent hydrocarbon having from 1 to 6 carbon atoms, a is at least 3 and b is at least 1; with an effective amount of a heteropoly catalyst having a Keggin structure, selected from the group consisting of heteropoly acids (III) having the formula $H_nXM_{12}O_{40}$, salts thereof and mixed acid-salts thereof, where X is $B^{+3}$, $Si^{+4}$, $Ge^{+4}$, or $P^{+5}$, M is $Mo^{+6}$ or $W^{+6}$ and n is 3, 4 or 5, as required for the valence of the heteropoly acid to equal 0, at a temperature ranging from about 23° C. to the boiling point of the siloxane polymer precursor.

The fluid comprises at least one siloxane polymer precursor. The siloxane polymer precursors useful in this invention can be described by formulas (I) and (II) provided above and are either commercially available or can be made by known methods.

Substituents R and R' in both (I) and (II) are individually selected from substituted or unsubstituted monovalent hydrocarbons having 1 to 6 carbon atoms. Examples of suitable monovalent hydrocarbon radicals that can be represented by R and R' include but are not limited to alkyl radicals such as methyl, ethyl, isopropyl or hexyl; alkenyl radicals such as vinyl, allyl or hexenyl; alkynal radicals such as propargyl; cycloaliphatic radicals such as cyclopentyl, cyclohexyl or cyclohexenyl; aromatic hydrocarbons such as phenyl; halogenated hydrocarbon or carbon radicals such as 3,3,3-trifluoropropyl, tridecafluoro-(1,1,2,2-tetrahydrooctyl)-1-methyl or perfluoroalkyl. R' can also be hydrogen.

R and R' are preferably methyl, vinyl, phenyl or 3,3,3-trifluoropropyl radicals. R' is also preferably hydrogen. Most preferably R and R' are each methyl radicals.

Subscripts a and b represent the number of —(RR'SiO)— repeating units in (I) and (II) respectively. The value of a is at least 3 and is preferably a positive integer from 3 to 6. The value of b is at least 1. Since this method will polymerize siloxane monomers as well as lower molecular weight siloxane oligomers and polymers into higher molecular weight siloxane polymers, the upper limit of b is limited primarily by one's ability to mix the fluid so it can contact the heteropoly catalyst. Preferably, the value of b is a positive integer from 2 to 100.

The term "siloxane polymer precursor" as used herein can comprise one type of cyclic siloxane or linear siloxane or it can comprise mixtures of one type of cyclic siloxane and linear siloxane or it can comprise mixtures of different types of cyclic siloxanes or linear siloxanes. Therefore the siloxane polymers prepared by this method can be homopolymers, copolymers or terpolymers.

Preferred siloxane polymer precursors are low molecular weight hydroxy-endblocked polydimethylsiloxane fluid and the cyclic siloxanes 3,3,3-trifluoropropyl(methyl)cyclic trimer $(CF_3(CH_2)_2MeSiO)_3$, $(Me_2SiO)_4$, $(Me_2SiO)_5$, $(Me_2SiO)_6$, $(HMeSiO)4$ and $(HMeSiO)_5$.

In addition to the siloxane polymer precursors, the fluid may also comprise other components including materials which will endblock the siloxane polymers formed by the method. The endblockers useful in this method are triorganosilyl endblockers that contain a radical of the formula $R^2R^3R^4Si$— wherein each $R^2$, $R^3$ and $R^4$ is independently selected from hydrogen, alkyl groups having from 1 to 6 carbon atoms, alkenyl groups having from 2–8 carbon atoms, aryl groups, arylalkyl groups and perfluoroalkylethyl groups having the formula $C_nF_{2n+1}CH_2CH_2$ where n is 1 to 6. The groups $R^2$, $R^3$ and $R^4$ can be the same or different as desired. Alkyl groups suitable as $R^2$, $R^3$ and $R^4$ in the method of this invention include methyl, ethyl, propyl, butyl, hexyl and octyl; alkenyl groups are exemplified by vinyl and 5-hexenyl; aryl groups are exemplified by phenyl and naphthyl; arylalkyl groups are exemplified by groups such as phenylmethyl, phenylpropyl and phenylhexyl and perfluoroalkylethyl groups include perfluoromethylethyl, perfluorodiethyl and perfluorooctylethyl.

The source of triorganosilyl endblocker radicals can be any material which under the reaction conditions used will form the triorganosilyl radical $R^2R^3R^4Si$—. Examples of triorganosilyl endblocker useful in this method include but are not limited to octamethyltrisiloxane, hexamethyldisiloxane, tetramethyl-3,3,3-trifluoropropyldisiloxane, trimethylchlorosilane and dimethylvinylchlorosilane. The preferred triorganosilyl endblocker is octamethyltrisiloxane.

The amount of triorganosilyl endblocker useful herein is dependent on the desired siloxane polymer chain length and can be determined experimentally by one skilled in the art. It is preferred to add the endblocker in an amount from 0.1 to 75 weight percent of the siloxane polymer precursors.

The fluid is contacted with an effective amount of a heteropoly catalyst having a Keggin structure. The heteropoly catalysts useful in this method are selected from the group consisting of heteropoly acids having the formula $H_nXM_{12}O_{40}$, salts thereof and mixed acid-salts thereof, where X is $B^{+3}$, $Si^{+4}$, $Ge^{+4}$, or $P^{+5}$, M is $Mo^{+6}$ or $W^{+6}$ and n is 3, 4 or 5 as required for the valence of the heteropoly acid to equal 0.

The portion of the formula represented by $(XM_{12}O_{40})^{q-}$ is described in the literature as a "heteropolyanion" having a Keggin structure, with X being described as a "heteroatom" and the metal-oxygen cluster $M_{12}O_{40}$ being described as an "isopolyanion". The heteropolyanions having a Keggin structure are important because they are stable and do not dissociate in solution and in solid form. Substituent M is a polyvalent metal and in the present method is preferably tungsten ($W^{+6}$) or molybdenum ($Mo^{+6}$). Substituent X can be $B^{+3}$, $S^{+4}$, $G^{+4}$, or and is preferably $P^{+5}$ and $Si^{+4}$. These heteropolyanions have open valences and are therefore charged species. The charge q of the heteropolyanion is dependent on the valences of X, M and O. The charge can be determined by multiplying the valences of the atoms associated with X, M and O by the value of the integer associated with that atom and adding the products together. For the heteropolyanion $(XM_{12}O_{40})^{q-}$ where X is $Si^{+4}$ and M is tungsten or molybdenum, the charge is equal to the sum of the valence of silicon (+4), 12 times the valence of M (+6) and 40 times the valence of oxygen (−2), which totals −4.

Since the heteropolyanion has a negative charge, it will associate with cations. When the cation is hydrogen, represented in the formula as H, a heteropoly acid is formed. The subscript n describes the number of hydrogens in a heteropoly acid required to neutralize the negative charge of the heteropolyanion. For this invention, n is 3, 4 or 5 depending on X. In the above example when X is $Si^{+4}$ and M is $W^{+6}$ or $Mo^{+6}$, 4 hydrogen atoms are needed to neutralize the −4 charge. Examples of heteropoly acids include but are not limited to phosphotungstic acid ($H_3PW_{12}O_{40}$), phosphomolybdic acid ($H_3PMo_{12}O_{40}$), silicotungstic acid ($H_4SiW_{12}O_{40}$) and silicomolybdic acid ($H_4SiMo_{12}O_{40}$).

If a cation other than hydrogen associates with the heteropolyanion, a heteropoly salt forms instead of a heteropoly acid. Examples of such cations include: alkali metals such as $Li^+$, $Na^+$, $K^+$, $Cs^+$ or $Rb^+$; alkaline earth metals such as $Ba^{+2}$, $Mg^{+2}$ or $Ca^{+2}$; and $R''_4N^+$, where each R'' is individually selected from the group consisting of hydrogen and monovalent hydrocarbon radicals having from 1 to 24 carbon atoms. Examples of the monovalent hydrocarbon radicals are the same as those given for R as well as dodecyl, octadecyl, octenyl, tolyl, xylyl, naphthyl, benzyl or gamma-tolylpropyl. Preferably, each R" is hydrogen. To form a neutral salt, the number of cations required can be 2, 3, 4 or 5, depending on X and the valency of the cation. Examples of typical salts include but are not limited to $(NH_4)_3PMo_{12}O_{40}$.

If both hydrogen and other cations, as described above for the heteropoly salt, are present with a heteropolyanion, a mixed heteropoly acid-salt results. To form a neutral mixed acid-salt the number of cations required can range from 2 to 5, including fractional numbers, depending on X and the valency of the cations. Examples of typical mixed acid-salts include but are not limited to $Cs_{2.5}H_{1.5}SiW_{12}O_{40}$ and $Cs_{2.5}H_{0.5}PW_{12}O_{40}$.

Heteropoly acids and mixed acid-salts are preferred heteropoly catalysts. More preferred are $H_3PW_{12}O_{40}$, $H_3PMo_{12}O_{40}$, $H_4SiW_{12}O_{40}$ and $Cs_{2.5}H_{1.5}SiW_{12}O_{40}$ and $Cs_{2.5}H_{0.5}PW_{12}O_{40}$. The heteropoly catalysts useful in this method are commercially available or can be prepared by known methods.

In a preferred method, the heteropoly catalyst is thoroughly dried prior to use. Various means may be used to dry the heteropoly catalyst and persons skilled in the art can determine the most convenient method to them. It was found however, that heating the heteropoly catalyst at 320° C. for about 3 hours provided a very active catalyst.

The heteropoly catalysts useful in this invention are solid materials which are not soluble in the siloxane polymer precursors or the siloxane polymers produced by the method. The heteropoly catalyst may be added to the fluid in solid form, dissolved in a suitable solvent or supported on an appropriate carrier.

Suitable solvents are those that will dissolve the heteropoly catalyst and in particular those that may assist in the transfer of protons and charges. Examples of suitable solvents are polar solvents such as water, acetone or alcohols. The heteropoly catalyst may be dissolved in the solvent prior to addition to the fluid or the solvent may be added to the fluid after addition of the heteropoly catalyst.

Methods for preparing heteropoly catalysts supported on carriers are known. In general, the heteropoly catalyst is dissolved in water and mixed under heat with a carrier until the water evaporates. Preferably, the supported catalyst is then dried by conventional methods. Examples of carriers include silica, alumina and carbon. A preferred carrier is silica. The amount of catalyst added depends on the loading desired. As used herein, "loading" means the weight percent of heteropoly catalyst in the support-heteropoly catalyst mixture. Typical loading for a heteropoly catalyst on a support is 0.1 to 75 weight percent. Preferred loading for a heteropoly catalyst on a support is 10 to 20 weight percent.

It is preferred to add the heteropoly catalyst in its solid form or supported on a carrier. Having the heteropoly catalyst in solid form or supported on a carrier simplifies removal of the catalyst, which is all that is required in order to terminate the polymerization process. The removal may be done, among other ways, by filtration. It is more preferred that the heteropoly catalyst be a heteropoly acid or mixed acid-salt supported on silica and in particular $H_3PW_{12}O_{40}$ supported on silica.

An effective amount of heteropoly catalyst is that amount which is necessary to catalyze the polymerization reaction and can range from about 0.0001 to 5 weight percent of the siloxane polymer precursor. Preferably, the amount of heteropoly catalyst used is from about 0.1 to 2 weight percent of the siloxane polymer precursor and most preferably the amount is from about 0.1 to 1 percent of the siloxane polymer precursor.

The critical step of this method requires that there be contact between the fluid and the heteropoly catalyst. This contact may be achieved, among other ways, by mixing the heteropoly catalyst with the fluid. This mixing may be done by conventional means, including stirring.

Generally, this polymerization reaction takes place at temperatures ranging from about 23° C. to the boiling point of the siloxane polymer precursors. The reaction could be conducted at temperatures below about 23° C. but the rate of reaction may become impractically slow. In addition, the reaction may be conducted above the boiling points of the siloxane polymer precursors if one used higher pressure or special apparatus to handle gaseous materials. Preferably, the polymerization reaction is conducted at temperatures ranging from about 80° C. to 150° C. and more preferably from 100° C. to 150° C.

Depending on a number of factors such as reaction temperature, whether the heteropoly catalyst is dried, the compatibility of the siloxane polymer precursor with the heteropoly catalyst, the solubility of the heteropoly catalyst in the fluid, the diffusion rate, the reactivity of the cyclic siloxane, i.e. whether the equilibrium constant favors the cyclic or linear siloxane and potential steric hindrance between the heteropoly catalyst and siloxane polymer precursor, the time for reaction may range from minutes to days.

The specific siloxane polymers formed by this new method depend on numerous factors including the siloxane polymer precursor used as a starting material, the endblocker added and time of reaction. Other than catalyzing the polymerization, the heteropoly catalyst is unaffected and does not become a part of the siloxane polymer. The heteropoly catalyst does not require neutralization in order to terminate the polymerization reaction but rather just needs to be removed from the mixture. It also appears, depending on the reaction conditions, that the siloxane polymers produced by this method may have reduced branching relative to that produced from polymerization of siloxane polymer precursors using standard acids and bases.

EXAMPLES

The following examples describe preferred embodiments of this method. The examples should not be interpreted as limiting the scope of the invention as defined in the claims. When used in the examples, "Vi" means vinyl, "Me" means methyl and "Ph" means phenyl.

For expediency, a number of experiments were terminated relatively quickly and no analytical data was obtained if it did not appear that a reaction had occurred during that time. Examples 10 and 11, in particular illustrate that the artisan will need to determine the optimum conditions for each siloxane polymer precursor and each heteropoly catalyst. Elements that need to be considered in addition to temperature and time that can change with each siloxane polymer precursor and each heteropoly catalyst include the compatibility of the siloxane polymer precursor with the heteropoly catalyst, the solubility of the heteropoly catalyst in the fluid, the diffusion rate, the reactivity of the cyclic siloxane, i.e. whether the equilibrium constant favors the cyclic or linear siloxane and even steric hindrance.

(A) Preparation of Phosphotungstic Acid ($H_3PW_{12}O_{40}$).

The phosphotungstic acid was prepared according to the method of Bailar Jr., J. C. In *Inorganic Syntheses*, ed. Booth, H. S., 1939; Vol 1, p.132.

(B) preparation of Phosphotunstic Acid ($H_3PW_{12}O_{40}$) Supported on Silica.

This preparation is an adaptation of the method published by Rocchiccioli-Deltcheff et. al., *J. Catal.* 1990, 126, 591. 10 g synthetic amorphous precipitated silica [surface area, 450 m2/g (BET method); particle size, 4.5 mm (Coulter counter method); pH, 7] were added to a 100 ml water solution containing 2 g dissolved $H_3PW_{12}O_{40}$. The resulting cloudy suspension was allowed to stir at about 55° C. until all the water evaporated. The white paste was dried in a vacuum oven overnight. A fluffy dried powder was obtained. The estimated loading of $H_3PW_{12}O_{40}$ was 16.7%.

(C) Preparation of Silicotungstic Acid.

The silicotungstic acid was prepared according to the method of North, E. O., In *Inorganic Syntheses*, ed. Booth, H. S., 1939; Vol 1, p.129.

Example 1

(a) In a 250 ml flask equipped with condenser, thermometer and stirring shaft, 100 g OH-endblocked polydimethylsiloxane (PDMS) fluid having a degree of polymerization (DP) of approximately 14 was heated to 100° C. Then, 0.1217 g (4.2×10−5 mol) $H_3PW_{12}O_{40}$ that had been dried at 320° C. for 3 hr was added, and the mixture stirred at 100° C. Half an hour after the addition of $H_3PW_{12}O_{40}$ the mixture became cloudy presumably due to generation of $H_2O$ which is not miscible with the PDMS fluid. Approximately 4 hr from the addition of $H_3PW_{12}O_{40}$ the viscosity of the mixture had increased substantially. A portion of the mixture was withdrawn from the reaction vessel, pressure filtered through a #1 Whitman paper to remove the catalyst, and characterized by $^{29}Si$ nuclear magnetic resonance (NMR) spectroscopy. The average DP was estimated from the ratio of the integrals of the resonances that correspond to the —OSi*$Me_2$O— nuclei to the resonance that corresponds to the terminal HO—Si*$Me_2$O— nuclei, to be approximately 352. The average chain length of the polymer was therefore approximately 354. The spectrum also revealed the presence of weak resonances at −65–67 ppm which correspond to "T" structures ($MeSiO_{3/2}$ branching) from the cleavage of Me—Si bonds.

(b) 190 g OH-endblocked PDMS fluid having a DP of approximately 14 was heated to about 82° C. in the apparatus described in Example 1(a) and 0.0292 g $H_3PW_{12}O_{40}$ added and the mixture stirred. The reaction was stopped after 6.5 hr since there was no obvious viscosity change of the mixture. $^{29}Si$ NMR characterization showed the presence of a few short PDMS linear segments having a DP of approximately 20 in addition to unreacted starting material.

(c) 103.5 g OH-endblocked PDMS fluid having a DP of approximately 14 was heated to about 80° C. in the apparatus described in Example 1(a). 0.1011 g $H_3PW_{12}O_{40}$ which had not been dried prior to use was added and the mixture stirred. After 3 hr the viscosity appeared unchanged and the reaction was terminated.

Example 2

100 g trifluoropropyl(methyl) trimer $(CF_3(CH_2)_2MeSiO)_3$ was heated under vigorous stirring in the apparatus described in Example 1(a). When the temperature of the solution reached 110° C., 0.1033 g (3.6×10−5 mol) $H_3PW_{12}O_{40}$ that had been dried at 320° C. for 3 hr was added and the mixture was allowed to reach 120° C. Within 40 min. the mixture attained a hazy appearance and increased in viscosity. The reaction was allowed to continue for a total of 5 hr. Analysis by $^{29}Si$ NMR spectroscopy showed the mixture was composed of 60% linear trifluoropropyl(methyl) polymer and 40% of starting trifluoropropyl(methyl) trimer. The average DP of the linear trifluoropropyl(methyl) polymer was estimated to be about 270.

The next day the polymerization reaction was re-initiated for 4 more hr giving a very viscous, creamy material. Based on the $^{29}Si$ NMR analysis the mixture was composed of about 99.5% linear trifluoropropyl(methyl) siloxane with an average DP of 832.

Example 3

100 g $(Me_2SiO)_4$ cyclic siloxane was heated to 120° C. in the apparatus described in Example 1(a) above with stirring and 2 g of $SiO_2$-supported $H_3PW_{12}O_{40}$ prepared as described in (B) above was added and produced a fine dispersion. In a few minutes the viscosity of the mixture increased substantially. The reaction was terminated after about 20 min. since stirring became ineffective and the polymer had the consistency of a gum. The unfiltered polymer mixture was characterized by $^{29}Si$ NMR spectroscopy to have an average DP of about 4600. Analysis by gel permeation chromatography (GPC) provided a number average molecular weight ($M_n$) of 2.316×10$^5$ for the mixture. The mixture composition was estimated from the areas of the peaks to be 73% linear PDMS, 6% short chain PDMS and 21% mixed cyclic siloxanes.

Example 4

(a) 101.1 g $(Me_2SiO)_4$ cyclic siloxane was heated to 120° C. in the apparatus described in Example 1(a) with stirring. Then 0.1215 g $H_3PMo_{12}O_{40}$ which had been dried for 3 hr at 320° C. was added. A color change from colorless to yellow to green occurred. Dried phosphomolybdic acid is yellow. The mixture was heated under 500 rpm stirring for 2 hr and 20 min with no apparent change in viscosity. When stirring was stopped the green $H_3PMo_{12}O_{40}$ quickly settled out of solution. The heating was interrupted overnight. Next day the mixture was sonicated for a few seconds with the intent to increase the dispersion of the catalyst, but no apparent change occurred. The mixture was heated to 140° C. and within minutes its viscosity increased and a thick lime colored suspension was obtained. The reaction was interrupted 20 min later since it was not possible to effectively stir the mixture. Based on $^{29}Si$ NMR data the average DP of the linear siloxane polymer in the mixture was about 6800. The amount of "T" structures ($MeSiO_{3/2}$ branching) was estimated from the integral at about −67 ppm to be about 14%. Analysis by gel permeation chromatography (GPC) provided a number average molecular weight ($M_n$) of 1.493×10$^5$ for the composition. The mixture composition was estimated from the areas of the peaks to be 78% linear PDMS, 3% short chain PDMS and 18% mixed cyclic siloxanes.

Example 5

(a) In a 250 ml flask equipped with a mechanical stirrer, thermometer, and a condenser so fitted at the top so as to be able to maintain a $N_2$ blanket, 150 g $(Me_2SiO)_4$ cyclic siloxane was heated to 120° C. Then, 0.15 g (4.68×10−5 mol) $Cs_{2.5}H_{1.5}SiW_{12}O_{40}$ that had been dried at 320° C. for 3 hr was added and the mixture stirred for 2 hr. During the first 10 min the liquid turned from whitish and slightly translucent to opaque and milky white. As no increase in viscosity was noted the temperature was raised to 140° C. within 10 min. The material was heated at 140° C. for 2.5 hr. After 1 hr the viscosity was observed to have increased moderately and continued to increase slowly during the remaining 1.5 hr. After bottling and standing overnight the material remained milky white and opaque with the catalyst being unable to settle out due to the high viscosity. $^{29}$Si NMR indicated a DP of about 3300 and approximately 0.21 "T" units (MeSiO$_{3/2}$) per polysiloxane chain.

(b) To 150 g of (Me$_2$SiO)$_4$ cyclic siloxane heated to 120° C. in the apparatus described in Example 5(a) above was added 0.15 g (3.6×10$^{-5}$ mol) of Cs$_{2.5}$H$_{0.5}$PW$_{12}$O$_{40}$ that had been dried for 3 hr at 320° C. Within 6 min the material was observed to be considerably more viscous. At 14 min the material was very difficult to stir and the experiment was terminated. Analysis by GPC (PDMS standard) showed a M$_n$ of 2.536×10$^5$ and 13.5 area percent cyclics.

(c) To 150 g of (Me$_2$SiO)$_4$ cyclic siloxane heated to 120° C. in the apparatus described in Example 5(a) above was added 0.15 g (5.29×10$^{-5}$ mol) (NH$_4$)$_3$PMo$_{12}$O$_{40}$ that had been dried 3 hr at 200° C. Initially the slurry was bright yellow then slowly developed a greenish cast. An increase in viscosity was noted after 13 min and became extremely viscous after 46 min and the experiment was terminated. $^{29}$Si NMR showed 24.9% (Me$_2$SiO)$_4$ remaining with no evidence of "T" (MeSiO$_{3/2}$) structures.

(d) To 150 g (Me$_2$SiO)$_4$ cyclic siloxane heated to 120° C. in the apparatus described in Example 5(a) above was added 0.15 g (4.4×10$^{-5}$ mol) Cs$_4$SiW$_{12}$O$_{40}$ that had been dried for 3 hr at 320° C. The material was heated at 120° C. for 2 hr, then 140° C. for 1 hr, then 150° C. for 1 hr and finally 160° C. for 0.5 hr. No change in viscosity was noted and the experiment was terminated. The inventors believe the compatibility of the salt and cyclic may have been reduced which contributed to slowness in the reaction.

Example 6

To a 100 ml flask fitted as the apparatus described in Example 5(a) above was added 50 g of a 50/50 mixture of (HMeSiO)$_4$ and (HMeSiO)$_5$ cyclic siloxanes. The methylhydrogen cyclics were heated to 100° C. at which time 0.1 g (3.5×10$^{-5}$ mol) H$_4$SiW$_{12}$O$_{40}$ were added. After 25 min the material became too difficult to stir terminating the experiment. $^{29}$Si NMR showed (HMeSiO)$_4$ (−32 to −32.6 ppm) and (HMeSiO)$_5$ (−34.2 to −34.5 ppm) to be greatly reduced and the appearance of methylhydrogen linears at −34.7 ppm. Allowed to sit more than one week the very viscous liquid was found to have turned to a very tough rubbery material.

Example 7

23.94 g (Me$_2$SiO)$_{x=4,5,6}$ cyclic siloxanes were mixed with 0.06 g (2.08×10$^{-5}$ mol) H$_4$SiW$_{12}$O$_{40}$ (dried at 320° C. for 3 hr) in a vial at ambient temperature and the viscosity of the mixture was monitored over a period of several days. The vial with the mixture was infrequently agitated. 3 wk from the beginning of the reaction a viscous liquid was obtained that took about 15 min. to flow upon inversion of the vial. The mixture had a viscosity of 4.5×10$^6$ Pa.s and a M$_n$ was estimated from GPC to be 2.2×10$^5$. It contained about 12.5% (Me$_2$SiO)$_{x=4,5, 6}$ and 87.5% polydimethylsiloxane. $^{29}$Si NMR spectrum showed no evidence of "T" structures (Me—SiO$_{3/2}$ groups).

Example 8

(a) A stock solution was prepared by mixing 1957.2 g (6.6 mol) (Me$_2$SiO)$_4$ cyclic siloxane and 42.8 g (0.17 mol) Me$_3$SiO(Me$_2$SiO) SiMe$_3$ having a viscosity of 1 Pa.s. Various experiments were done using flasks equipped with a magnetic stirrer, glass stirring gland sealed at the top with a rubber septum (for the removal of samples via a glass syringe and large bore needle), a thermometer connected to a Therm-o-watch for temperature control and a water condenser. For each experiment 300 g of the stock solution was added and kept under a blanket of N$_2$ gas and 0.1 weight percent of either H$_4$SiW$_{12}$O$_{40}$ or H$_3$PW$_{12}$O$_{40}$ was also added. The drying conditions for the catalyst and heating temperatures were varied and the results provided in Table 1.

(b) Same procedure was followed as in Example 8(a) above except a comparison catalyst trifluoromethanesulfonic acid, CF$_3$SO$_3$H was used, also in an amount to give 0.1 weight percent. Results are provided in Table 1.

TABLE 1

| Heteropoly Catalyst | Drying conditions | Temp (°C.) | Time (hr) | viscosity (m$^2$/sec) | DP$^a$ | % cyclics$^a$ |
|---|---|---|---|---|---|---|
| H$_4$SiW$_{12}$O$_{40}$ | 3 hr at 320° C. | 80 | 5.2 | partial gel | — | — |
| H$_4$SiW$_{12}$O$_{40}$ | 3 hr at 320° C. | 100 | 5.5 | — | 124 | 36 |
| H$_4$SiW$_{12}$O$_{40}$* | 3 hr at 320° C. | 120 | 5.5 | 1.82 | 174 | 8 |
| H$_4$SiW$_{12}$O$_{40}$ | 3 hr at 320° C. | 150 | 36 | 0.36 | 94 | 34 |
| H$_3$PW$_{12}$O$_{40}$ | as made | 120 | 5.5 | 0.21 | 55 | 44 |
| H$_3$PW$_{12}$O$_{40}$ | 24 hr at 125° C. | 120 | 5.5 | 0.03 | — | — |
| H$_3$PW$_{12}$O$_{40}$** | 3 hr at 320° C. | 120 | 5.5 | 2.20 | 177 | 5 |
| FC-28$^b$ | N/A | 70 | 4.0 | 2.36 | 168 | 4 |

$^a$Derived from $^{29}$Si NMR data
$^b$Trifluoromethanesulfonic acid, CF$_3$SO$_3$H (comparative example)
*Mn determined by GPC to be 8.9 × 10$^3$
**Mn determined by GPC to be 9.9 × 10$^3$ (c) 300 g (1.01 mol) (Me$_2$SiO)$_4$ cyclic siloxane and 0.3 g (1.04×10$^{-4}$ mol) H$_4$SiW$_{12}$O$_{40}$ that had been dried 3 hours at 320° C. were mixed in the apparatus described in Example 8(a) above having the modification of the insertion of a glass pipette into a glass stirring gland. The pipette was used to estimate the increase in viscosity during the experiment, without having to withdraw samples from the solution. The material was heated to 120° C. for about 1.5 hr at which time it became too viscous to stir.

Example 9

(a) 300 g of a 3.5 m$^2$/sec mixture of PDMS linears and cyclic siloxanes were placed in the apparatus described in Example 8(a) above and kept under N$_2$ blanket. After heating at 150° C., 1 g (3.5×10⁻⁴ mole) $H_3PW_{12}O_{40}$ was added and heating was maintained for 4 hr. Table 2 describes the results obtained.

(b) The procedure described in Example 9(a) was used except that 4.96 g of an acid washed montmorillonite clay were added instead of the heteropoly catalyst. This example provides comparison data as shown in Table 2.

TABLE 2

| Catalyst | Temp (°C.) | Time (hr) | vis. (m²/sec) | DPª | % cyclicsª | $[M_n]$ ×10³ | $[M_w/M_n]$ | silanol content (ppm) | "T" branches (ppm) |
|---|---|---|---|---|---|---|---|---|---|
| starting material | | | | 58 | 5 | 7.1 | 2.0 | 866.54ᵇ | 2474ᵈ |
| clay | 150 | 4 | 4.22 | 132 | 7 | 9.2 | 3.5 | 33.74 | 9303 |
| $H_3PW_{12}O_4$ᶜ | 150 | 4 | 2.81 | 163 | 6 | 8.7 | 2.7 | 97.01 | 4563 |

ªEstimated from ²⁹Si NMR.
ᵇAverage of two measurements (873.59, 859.50)
ᶜDried for 3 hr at 320° C.
ᵈ±8%.

Example 10

(a) To a 2 dram vial was added <0.1 g (<5.3×10⁻⁴ mol) $(NH_4)_3PMo_{12}O_{40}$ that had been dried 3 hr at 200° C., and approximately 3 g of $(ViMeSiO)_4$ cyclic siloxane and heated for 12–15 hr at 55° C. An increase in viscosity was noted with ²⁹Si NMR showing 26.3% linear —$(SiMeViO)_n$— species formed. No further increase in viscosity was noted after standing at room temperature for several days.

(b) 125 g $(ViMeSiO)_4$ cyclic siloxane was heated at 120° C. using the apparatus described in Example 5(a) above and 2 g of silica supported $H_3PW_{12}O_{40}$ prepared as described in (B) above was added. The catalyst, a puffy white material turned a light brown color when it was added and turned darker with time. The material was heated sequentially for 1 hr each at 120° C., 140° C. and 150° C. with no observed change in viscosity. The experiment was then terminated.

(c) 125 g $(ViMeSiO)_4$ cyclic siloxane was heated at 120° C. using the apparatus described in Example 5(a) above and 0.25 g (8.69×10⁻⁵ moles) of $H_4SiW_{12}O_{40}$ that had been dried at 320° C. for 3 hours was added. After heating at 120° C. for 2 hr with no apparent change in viscosity, the temperature was increased to 140° C. and held for 1 hr. No increase in viscosity was noted and the experiment was terminated.

Example 11

(a) 150 g of $(MePhSiO)_4$ cyclic siloxane was added to the apparatus described in Example 5(a), heated to 120° C. and 0.3 g (1.04×10⁻⁴ mol) of $H_4SiW_{12}O_{40}$ which had been dried 3 hours at 320° C. was added. The mixture was heated for almost 4 hr at 120° C. without any apparent increase in viscosity. During this time the mixture turned from whitish hazy to faint green to green then very gray in color. The temperature was then increased to 130° C. for 0.5 hr and then 140° C. for 35 min. No increase in viscosity was noted and the experiment was terminated.

(b) 100 g of mixed phenylmethyl cyclic siloxanes were heated to about 150° C. in the apparatus described in Example 1(a) under stirring. To the hot liquid, 2 g of silica supported $H_3PW_{12}O_{40}$ prepared in a manner similar to that described in (B) above and having a 20% loading was added and the mixture continued to heat and stir. The reaction was terminated after 6 hr and no increase in viscosity was observed.

We claim:

1. A method of forming siloxane polymers, the method comprising contacting a fluid comprising at least one siloxane polymer precursor selected from the group consisting of cyclic siloxanes (I) having the formula $(RR'SiO)_a$ and linear siloxanes (II) having the formula

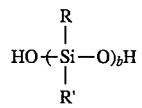

where R is a substituted or unsubstituted monovalent hydrocarbon having from 1 to 6 carbon atoms, R' is hydrogen or a substituted or unsubstituted monovalent hydrocarbon having from 1 to 6 carbon atoms, a is at least 3 and b is at least 1; with an effective amount of a heteropoly catalyst having a Keggin structure, selected from the group consisting of heteropoly acids (III) having the formula $H_nXM_{12}O_{40}$, salts thereof and mixed acid-salts thereof, where X is $B^{+3}$, $Si^{+4}$, $Ge^{+4}$, or $P^{+5}$, M is $Mo^{+6}$ or $W^{+6}$ and n is 3, 4 or 5, as required for the valence of the heteropoly acid to equal 0, at a temperature ranging from about 23° C. to the boiling point of the siloxane polymer precursor, to form siloxane polymers.

2. The method of claim 1, wherein the effective amount of heteropoly catalyst is from about 0.0001 to about 5 weight percent based on the siloxane polymer precursor.

3. The method of claim 2, wherein the heteropoly catalyst is a heteropoly acid or a heteropoly mixed acid salt.

4. The method of claim 3, wherein the heteropoly catalyst is dried prior to contacting the siloxane polymer precursor.

5. The method of claim 4, wherein R is a vinyl radical, a methyl radical, a phenyl radical or a 3,3,3 trifluoropropyl radical and R' is R or hydrogen.

6. The method of claim 5, wherein R is a methyl radical or a 3,3,3 trifluoropropyl radical; R' is R or hydrogen; a is a positive integer from 3 to 7 and b is a positive integer from 2 to 100.

7. The method of claim 6, wherein the temperature is from 80° to 150° C.

8. The method of claim 7, wherein the effective amount of heteropoly catalyst is from about 0.1 to 2 weight percent based on the siloxane polymer precursor.

9. The method of claim 8, wherein the heteropoly catalyst is selected from $H_3PW_{12}O_{40}$, $H_3PMo_{12}O_{40}$, $H_4SiW_{12}O_{40}$, $H_4SiMo_{12}O_{40}$, $(NH_4)_3PMo_{12}O_{40}$, $Cs_{2.5}H_{1.5}SiW_{12}O_{40}$ and $Cs_{2.5}H_{0.5}PW_{12}O_{40}$.

10. The method of claim 9, wherein the heteropoly catalyst is supported on a carrier with a loading of from 0.1 to 75 weight percent.

11. The method of claim 10, wherein the heteropoly catalyst is $H_5PW_{12}O_{40}$ supported on silica at a loading of 10 to 20 weight percent.

12. The method of claim 11, wherein a is 4, 5 or 6.

13. The method of claim 12, wherein R and R' are each methyl radicals.

14. The method of claim 9, wherein R and R' are each methyl radicals and a is 4, 5 or 6.

15. The method of claim 14, wherein the siloxane polymer precursor is the cyclic siloxane (I).

16. The method of claim 14, wherein the fluid further comprises a triorganosilyl endblocker.

\* \* \* \* \*